(12) United States Patent
Ross et al.

(10) Patent No.: US 9,299,036 B2
(45) Date of Patent: Mar. 29, 2016

(54) LIFE PATTERN DETECTION

(75) Inventors: Mark A. Ross, San Carlos, CA (US); Zongde Qiu, San Jose, CA (US); David Jonq Wang, Palo Alto, CA (US); Conway Thomas Chen, West Los Angeles, CA (US); Ronald Jen-Chuan Chwang, Los Altos Hills, CA (US)

(73) Assignee: STRIIV, INC., Redwood City, CA (US)

( * ) Notice: Subject to any disclaimer, the term of this patent is extended or adjusted under 35 U.S.C. 154(b) by 792 days.

(21) Appl. No.: 13/601,683

(22) Filed: Aug. 31, 2012

(65) Prior Publication Data

US 2013/0054505 A1 Feb. 28, 2013

Related U.S. Application Data

(60) Provisional application No. 61/529,764, filed on Aug. 31, 2011, provisional application No. 61/529,664, filed on Aug. 31, 2011, provisional application No. 61/529,674, filed on Aug. 31, 2011, provisional application No. 61/529,657, filed on Aug. 31, 2011, provisional application No. 61/529,780, filed on Aug. 31, 2011, provisional application No. 61/529,805, filed on Aug. 31, 2011, provisional application No. 61/529,770, filed on Aug. 31, 2011.

(51) Int. Cl.
*H03F 1/26* (2006.01)
*G06Q 10/00* (2012.01)
*G06Q 30/02* (2012.01)
*G06Q 50/12* (2012.01)
(Continued)

(52) U.S. Cl.
CPC .............. *G06Q 10/00* (2013.01); *G06Q 30/02* (2013.01); *G06Q 30/0282* (2013.01); *G06Q 50/12* (2013.01); *H04L 67/12* (2013.01); *G06F 19/3481* (2013.01); *G09B 19/0092* (2013.01); *H04N 9/87* (2013.01)

(58) Field of Classification Search
CPC ... G06Q 30/02; G06Q 50/12; G06Q 30/0282; G09B 19/0092; H04N 9/87; G06F 19/3481
USPC .................... 702/189; 340/506, 573.2, 539.1, 340/539.11, 540; 706/46, 12
See application file for complete search history.

(56) References Cited

U.S. PATENT DOCUMENTS 5,890,128 A 3/1999 Diaz et al.
6,811,516 B1 11/2004 Dugan
(Continued)

FOREIGN PATENT DOCUMENTS

CN 101741557 A * 6/2010
CN 102068260 A 5/2011
(Continued)

OTHER PUBLICATIONS

International Search Report dated Mar. 4, 2013 in Application No. PCT/US2012/053522.
(Continued)

*Primary Examiner* — Carlos S Tsai
(74) *Attorney, Agent, or Firm* — Maschoff Brennan

(57) ABSTRACT

An example embodiment includes a life pattern detection system. The life pattern detection system includes a sensor, a data acquisition device, and a first processor. The sensor is configured to monitor actions of a user. The data acquisition device is configured to harvest signals from the sensor and produce sensor data. The first processor is configured to receive the sensor data and background data, and to execute a life pattern application including a first series of analytical steps that determines a predictable set of actions from the sensor data and the background data.

20 Claims, 7 Drawing Sheets

(51) Int. Cl.
*H04L 29/08* (2006.01)
*G06F 19/00* (2011.01)
*H04N 9/87* (2006.01)
*G09B 19/00* (2006.01)

(56) References Cited

U.S. PATENT DOCUMENTS

| | | | |
|---|---|---|---|
| 7,980,997 | B2 | 7/2011 | Thukral et al. |
| 2003/0005113 | A1* | 1/2003 | Moore ................ 709/224 |
| 2006/0183980 | A1 | 8/2006 | Yang |
| 2009/0171775 | A1* | 7/2009 | Cashion et al. ........... 705/14 |
| 2009/0210373 | A1 | 8/2009 | Yu et al. |
| 2009/0259865 | A1 | 10/2009 | Sheynblat et al. |
| 2010/0013778 | A1 | 1/2010 | Liu et al. |
| 2010/0111004 | A1* | 5/2010 | Yi et al. ................ 370/329 |
| 2010/0241464 | A1 | 9/2010 | Amigo et al. |
| 2010/0241504 | A1 | 9/2010 | Bolt |
| 2010/0274617 | A1 | 10/2010 | Suomela et al. |
| 2010/0280935 | A1* | 11/2010 | Fellowes et al. .......... 705/35 |
| 2011/0098928 | A1 | 4/2011 | Hoffman et al. |
| 2011/0185199 | A1 | 7/2011 | Hung et al. |
| 2011/0230732 | A1* | 9/2011 | Edman et al. ............ 600/301 |
| 2014/0149235 | A1* | 5/2014 | Gilley et al. ............. 705/15 |

FOREIGN PATENT DOCUMENTS

| | | |
|---|---|---|
| DE | 10 2005 008 386 A1 | 8/2006 |
| EP | 1 879 096 A2 | 1/2008 |
| EP | 2 018 825 A1 | 1/2009 |
| KR | 10-2001-0077459 A | 8/2001 |
| WO | 01/82783 A2 | 11/2001 |
| WO | 01/82783 A3 | 11/2001 |
| WO | 20041032715 A2 | 4/2004 |
| WO | 20041032715 A3 | 4/2004 |
| WO | 2005/038693 A1 | 4/2005 |
| WO | 2011/080603 A2 | 7/2011 |

OTHER PUBLICATIONS

Written Opinion of the International Searching Authority dated Mar. 4, 2013 in Application No. PCT/US2012/053522.
International Search Report dated Feb. 1, 2013 in Application No. PCT/US2012/053521.
Written Opinion of the International Searching Authority dated Feb. 1, 2013 in Application No. PCT/US2012/053521.
Extended European Search Report dated May 12, 2015 as received in Application No. 12 82 8825.
EP Office Action dated Jan. 22, 2016 as received in Application No. 12 828 825.5.

* cited by examiner

LIFE PATTERN DETECTION

CROSS-REFERENCE TO RELATED APPLICATIONS

This application claims the benefit of and priority to U.S. Provisional Application Nos. 61/529,764; 61/529,664; 61/529,674; 61/529,657; 61/529,780; 61/529,805; and 61/529,770 all filed on Aug. 31, 2011 and all of which are incorporated herein by reference in their entireties.

FIELD

Some embodiments described herein relate to determining life patterns. Specifically, some example embodiments use sensors operably configured to obtain independent signals, which are processed to determine life patterns.

BACKGROUND

Pedometers and other mobile devices have become a convenient way for users to track caloric consumption during the course of ordinary activities or exercise. Pedometers, for example, may be secured to the user's body and track the number of steps the user takes during the course of a day. Many pedometers include a single accelerometer and simply display the number of steps to the user upon completion of an activity. Similarly, some mobile devices may come equipped with global position signal (GPS) receivers. The GPS receivers may interface with an application on the mobile device such that the user may track a distance covered while running or biking. The pedometer and the mobile device may simply reset each time the user begins a new activity.

Additionally, the pedometer and the mobile devices may not interface with the user, may provide limited data, and may not interface with other computing devices. The pedometer and the mobile device may therefore fail to provide the user with continuity across multiple activities or to provide an individualized experience for the user.

The subject matter claimed herein is not limited to embodiments that solve any disadvantages or that operate only in environments such as those described above. Rather, this background is only provided to illustrate one example technology area where some embodiments described herein may be practiced.

SUMMARY

The object and advantages of the embodiments will be realized and achieved at least by the elements, features, and combinations particularly pointed out in the claims.

An example embodiment includes a life pattern detection system. The life pattern detection system includes a sensor, a data acquisition device, and a first processor. The sensor is configured to monitor actions of a user. The data acquisition device is configured to harvest signals from the sensor and produce sensor data. The first processor is configured to receive the sensor data and background data, and to execute a life pattern application including a first series of analytical steps that determines a predictable set of actions from the sensor data and the background data.

Another example embodiment includes a multi-function device. The multi-function device includes an internal sensor, a signal acquisition processor, a first processor, a second processor, and a display. The internal sensor is configured to sense actions of a user. The signal acquisition processor is configured to harvest sensor data from the internal sensor. The first processor is configured to determine a predictable set of actions from the sensor data. The second processor is configured to determine a modification suggestion to alter an action included in the predictable set of actions and to generate an incentive corresponding to the modification suggestion. The display is configured to display the modification suggestion and the incentive to the user.

Another example embodiment includes a method of determining a life pattern for the purpose of altering behavior. The method includes collecting multiple signals from multiple sensors. The method also includes detecting from the multiple signals a life pattern of a user. The life pattern constitutes a predictable set of actions. The method also includes determining a modification suggestion. The modification suggestion includes a proposed modification to at least one of the actions in the life pattern. The method also includes incentivizing the modification suggestion. The method also includes communicating the modification suggestion and a corresponding incentive to the user.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

It is to be understood that both the foregoing general description and the following detailed description are exemplary and explanatory and are not restrictive of the invention, as claimed.

BRIEF DESCRIPTION OF THE DRAWINGS

To further clarify the above and other advantages and features of some embodiments, a more particular description will be rendered by reference to specific embodiments thereof which are illustrated in the appended drawings. It is appreciated that these drawings depict only typical embodiments and are therefore not to be considered limiting of its scope. The invention will be described and explained with additional specificity and detail through the use of the accompanying drawings in which.

DESCRIPTION OF EMBODIMENTS

Some example embodiments relate to use of sensors to detect life patterns. These life patterns include routine behaviors that become a predicable set of actions. Following the determination of the life pattern, the actions can be analyzed to generate modification suggestions and a corresponding set of incentives. Through completion of the modification suggestions, the user may receive the incentive and/or another benefit.

Figure 1A:
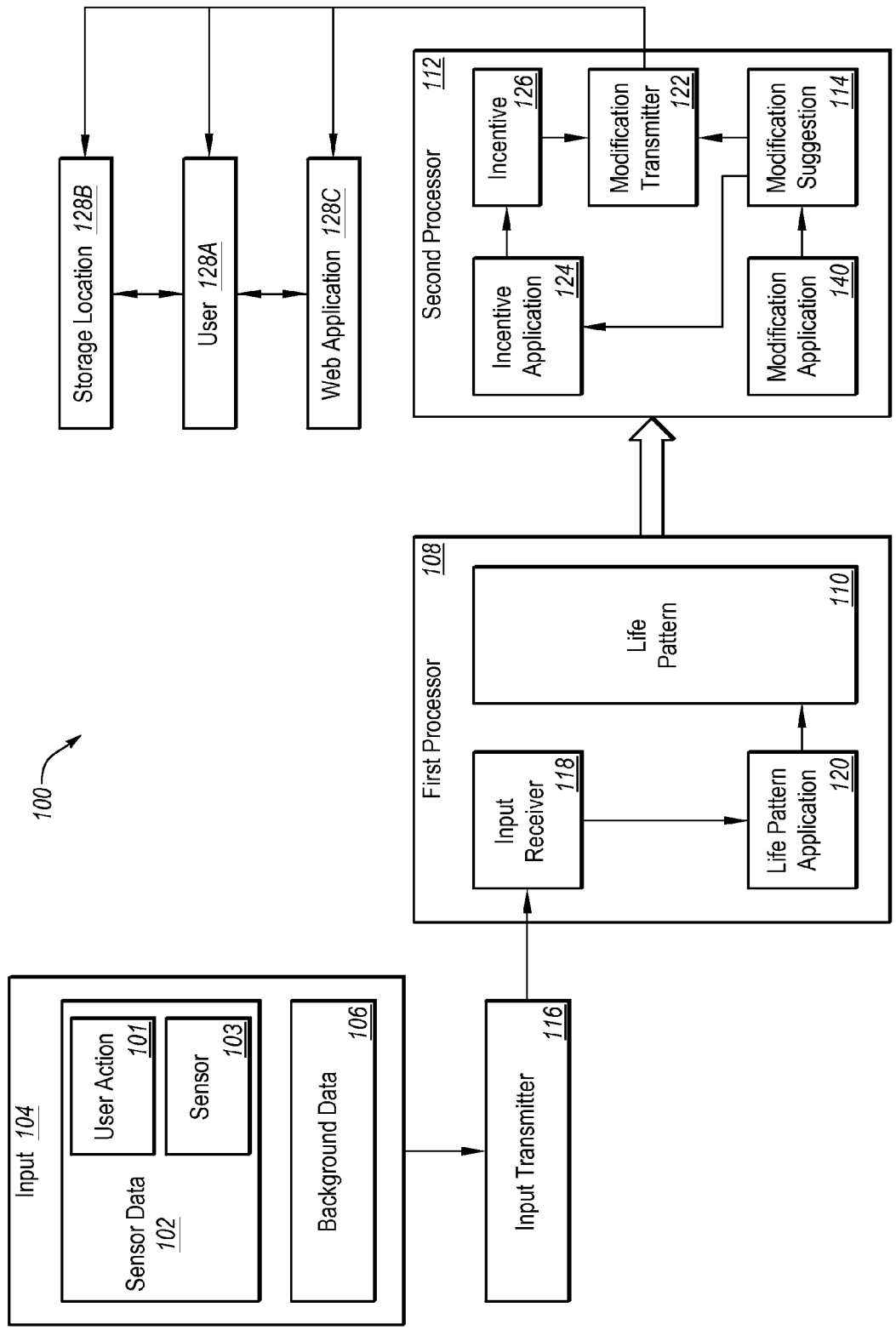
FIG. 1A illustrates an example life pattern detection system.

FIG. 1A illustrates an example life pattern detection system 100. In the life pattern detection system 100, a first processor 108 may receive input 104 from an input transmitter 116. Types of input 104 may include sensor data 102 and background data 106. The sensor data 102 may be generated from signals of one or more sensors 103. The sensor data 102 may represent user actions 101 or some portion thereof. For example, sensor data 102 may include the number of steps measured by a sensor 103 such as an accelerometer. The sensor data 102 may be provided as input 104 according to a sensor and signal acquisition system (not shown). Example architectures of sensor and signal acquisition systems are discussed with reference to FIGS. 2A and 2B below.

The input 104 may also include the background data 106. The background data 106 refers to input 104 not produced by the sensors 103 monitoring the user actions 101. Examples of the background data 106 may include, but is not limited to, appointments in calendars, weather reports, locations of other users, and scheduled community events. The background data 106 may also include manually entered information such as user-specific fitness goals, biographical statistics, personal demographics, preferential settings, local and network game applications, and fitness program subscriptions.

The life pattern detection system 100 may include the input transmitter 116. Generally, the input transmitter 116 communicates the input 104, which may include the sensor data 102 and/or the background data 106, from the location the input 104 originates to the first processor 108. In some embodiments, the input transmitter 116 may include multiple individual transmitters with a variety of capabilities and structures dependent on the architecture of the sensors 103 and the types of background data 106. Examples of input transmitters 116 may include, but are not limited to, transmitters located at sensors 103 that transmit sensor signals via a computer or electrical network; manual input; device interface with a network cloud; downloading application software; and manual or automated synchronization between an acquisition device (discussed below) and the first processor 108.

For example, the input 104 may include the sensor data 102 and the background data 106. The sensor data 102 may include a global positioning system (GPS) signal received by a GPS receiver incorporated in a cellular telephone. The background data 106 may include a weather report published on a public website. In this example, the input transmitter 116 may include the cellular telephone transmitting the GPS coordinates to the first processor 108 as well as the software application that monitors the public website to download weather information included in the weather report.

The first processor 108 may include an input receiver 118. Generally, the input receiver 118 may be configured to receive the input 104 transmitted to the first processor 108 by the input transmitter 116. Similar to the input transmitter 116, the input receiver 118 may include multiple individual receivers with a variety of capabilities and structures, which may depend on the architecture of the sensors 103 and the types of background data 106, for instance. In some embodiments, the input transmitter 116, input receiver 118, or some functions described with reference thereto may be incorporated in one or more data acquisition devices and/or data acquisition processors. Some details of such data acquisition devices and/or data acquisition processors are provided below.

In some embodiments, the input transmitter 116 may be operably coupled to the sensor 103. Thus, the sensor 103 may be an independent, autonomous sensor. The autonomous sensor may monitor the user actions 101 and transmit sensor data 102 indicating the user action 101. For example, the autonomous sensor may include a heart rate monitor or a galvanic skin sensor including the input transmitter 116.

In these and other embodiments, the life pattern detection system 100 may also include a server (not shown). The server may include a server input receiver that may be similar to or identical to the input receiver 118. The server may be configured to receive sensor data 102 collected by the sensor 103 and/or the autonomous sensor. The server may be further configured to analyze the received sensor data 102 as described below with respect to the first processor 108 and/or the second processor 112. The server may then communicate results from the analysis to one or more users 128A, one or more of the first processor 108 and/or the second processor 112, one or more other servers, a storage location 128B, a web application 128C, or one or more devices.

Alternatively, the server may receive the sensor data 102 from the sensor 103 or the autonomous sensor. Following reception of the sensor data 102, the server may store the sensor data 102 for some period, thereby allowing a greater amount of sensor data 102, optionally from multiple users, to accumulate. The server may then sync with the first processor 108 and communicate the sensor data 102, or some portion thereof, to the first processor 108.

The communication between the first processor 108 and the server may include communication of the sensor data 102 from multiple users and communication of analysis results. In addition, the communication between the first processor 108 and the server may enable analysis of sensor data 102 by the first processor 108 at the server. The communication between the first processor 108 and the server may be controlled by relative locations of the first processor 108 and/or the server, preset passwords, permissions, or any other mechanism that may enable secure communication.

The first processor 108 (which may be included in the server discussed above or in another device) may be configured to execute a life pattern application 120. The life pattern application 120 may be stored in a memory or other computer-readable storage medium (not shown). The life pattern application 120 may collect the input 104 received by the input receiver 118. Through a series of analytical steps, the life pattern application 120 may analyze the input 104 to generate one or more life patterns 110. Examples of the analytical steps may include, but are not limited to, organizing the input 104 into types of sensor signals, time sequencing the input 104, sequencing the input 104 by positional coordinates, extracting signals consistent with a movement classification such as walking or driving, fitting sensor data 102 to background data 106 such as calendar events, establishing and monitoring for repeating and/or predictable patterns as in daily or weekly actions, evaluating the input 104 from other users such as positional information to create social proximities, and eliminating impossible or improbable results or the input 104 that is erroneous. An example of generating a life pattern 110 is described with respect to FIG. 3.

The first processor 108 may be integrated into the server or a personal electronic device (PED). Some examples of the PED may include a pedometer, cellular/mobile/smart telephone, tablet personal computer, laptop computer, personal digital assistant, satellite based positioning system, or any equivalent device. Optionally, the first processor 108, or functions described with respect to the first processor 108 may be distributed between a PED and the server such that some of the analytical steps are performed at the PED and some of the analytical steps are performed at the server. The results from each may be combined to generate a life pattern 110.

In some embodiments, the first processor 108 includes two processors, including a microcontroller and a main processor. In this and other embodiments, the microcontroller may operate at a lower power consumption level than the main processor. The microcontroller may additionally be configured to monitor a subset of sensors 103. During this monitoring, the main processor sleeps, reducing its power consumption level. The microcontroller may be programmed with a software application such that, at some threshold signal from any of the subset of sensors 103, the microcontroller triggers the main processor, restoring the main processor's active capabilities to process the sensors' signal. Through this configuration, power consumption of the first processor 108 may be conserved.

The life pattern 110 may be communicated to a second processor 112. The second processor 112 may be a separate processor or may be an additional application or applications run on the first processor 108. In some embodiments, the second processor 112 executes a modification application 140 on the life pattern 110 generated by the first processor 108. The modification application 140 generates modification suggestions 114. Examples of steps that may be performed by the modification application 140 may include, but are not limited to, organizing the life pattern 110 into identifiable actions, determining whether substitute actions exist, grouping similar users together, downloading additional background data 106 relevant to the physical setting such as building floor plans or mass transit maps, requesting additional information, or examining the user's personal goals.

In some embodiments, the second processor 112 may additionally execute an incentive application 124. The incentive application 124 may generate one or more incentives 126 based on the life pattern 110 generated by the first processor 108 and/or the modification suggestions 114. The one or more incentives 126 may correspond to the modification suggestions 114.

In some embodiments, the incentives 126 may conform to a game application, a virtual economy, a personal incentive program, or interface with a social networking application. The game applications may include local or network games that apply the completion of the incentives 126 as points or achievements. The game may optionally include inter-participant or intra-participant competition. Similarly, the virtual economy may reward the completion of the incentives 126 with virtual currency that may be exchanged within the virtual economy for virtual rewards or may be exchanged in the real world for goods or services. The personal incentive program may be customized to a particular user or group of users or may be a predetermined program.

In general, in the life pattern detection system 100 the modification suggestions 114 and the incentives 126 seek to encourage an increase in physical activities and create health benefits such as improved physical condition. Alternatively, the modification suggestions 114 and incentives 126 may incorporate commercial sponsorship. An example of a commercial sponsorship may be a modification suggestion 114 to eat at a specific restaurant located along a route indicated in a life pattern 110. An example of the generation of a modification suggestion 114 and the incentives 126 is described with respect to FIG. 4.

Similar to the first processor 108, the second processor 112 may be integrated into a centralized server or a PED. Optionally, the second processor 112 may be distributed between a PED and a server such that some modification application steps are performed at the PED and some modification application steps are performed at the server. The results from each of the PED and the server may be combined to generate a modification suggestion 114 and/or incentives 126.

The second processor 112 may include a modification transmitter 122 which transmits the modification suggestion 114 and/or the incentives 126. The modification transmitter 122 may transmit the modification suggestion 114 and/or the incentives 126 to a user 128A, a storage location 128B, a web application 128C, or some combination thereof, for example. The structure and configuration of the second processor 112 may dictate the structure of the modification transmitter 122 and/or where the modification suggestion 114 and/or the incentives 126 are transmitted. For example, the modification transmitter 122 may include, but is not limited to, an optical or digital transmitter located at the server such as a wireless transmitter or an application that stores the modification suggestion 114 and/or incentives 126 such that the user 128A may interface with the storage location 128B. Additionally or alternatively, the modification transmitter 122 may include an application that generates an email, that updates an internet website or social networking application which can be password secured or personalized to the user 128A.

The social networking application may include a capability to post or otherwise publicize and optionally track the completion of modification suggestion 114 and/or the completion of the incentives 126. In the social networking application, multiple users may form an online community, thereby enabling access to posts of the modification suggestions 114 and/or the incentives 126 received or completed by each of the users included in the online community.

Additionally or alternatively, the modification transmitter 122 may be a telephone-based apparatus that transmits the modification suggestion 114 and/or the incentive 126 to the user 128A via SMS text, MMS text, or places a phone call to the user 128A, or the like or any combination thereof. In some embodiments, the completion of incentives 126 and/or modification suggestions 126 may be communicated to a group of users. The communication to the group may be accomplished through any form of electronic or network communication including, but not limited to, SMS text, MMS text, email, server calls, posted messages on one or more websites, posted messages on one or more networking applications, or any combination thereof. Similar to the online community discussed above, the group of users may receive the SMS text or the MMS text, etc. indicating completion of the modification suggestion 114 and/or the incentive 126 of other users in the group.

In some example embodiments, a hybrid synchronous interface with the user may dictate the timing of the transmission of modification suggestions 114 and/or the incentives 126 by the modification transmitter 122. The hybrid synchronous interface may refer to two temporal interactions, periodic and real time, when the user receives or has access to the modification suggestions 114 and the incentives 126. First, the user may receive or have access on a periodic schedule. The periodic schedule may be utilized when the life pattern 110 includes actions that occur over a greater time period such as a month or year. An example may be overall caloric consumption for the month. The user may receive or obtain access to the modification suggestion 114 "eat 10% more green vegetables to receive 1000 Striiv energy" which may be transmitted at the beginning of the month.

In addition, with the hybrid synchronous interface the user may receive real time modification suggestions 114 and/or incentives 126 for the life patterns 110 as individual actions occur or are about to occur. For example, a life pattern 110 may include eating every weekday in the office cafeteria. When the life pattern 110 is triggered by some initial action or the user's lunchtime, the modification suggestion 114 and the incentives 126 "eat at the market today receive 10 Striiv energy" may be transmitted. As in this example, the periodic and real time modification suggestions 114 may relate to the same overall goal. Alternatively, the periodic and real time modification suggestions 114 may not be related.

In some embodiments, the user 128A may carry multiple PEDs, each of which may include one or more sensors 103, the first processor 108, the second processor 112, or some combination thereof. In these and other embodiments, each PED may independently receive and process input 104 to generate life patterns 110. Additionally or alternatively, the input 104 received at the separate PEDs may be aggregated and correlated to determine that the separate PEDs are receiving the same physical stimulus and are therefore on the same user 128A. For instance, the input 104 may be aggregated at one of the PEDs, or at a separate server, or the like.

Figure 1B:
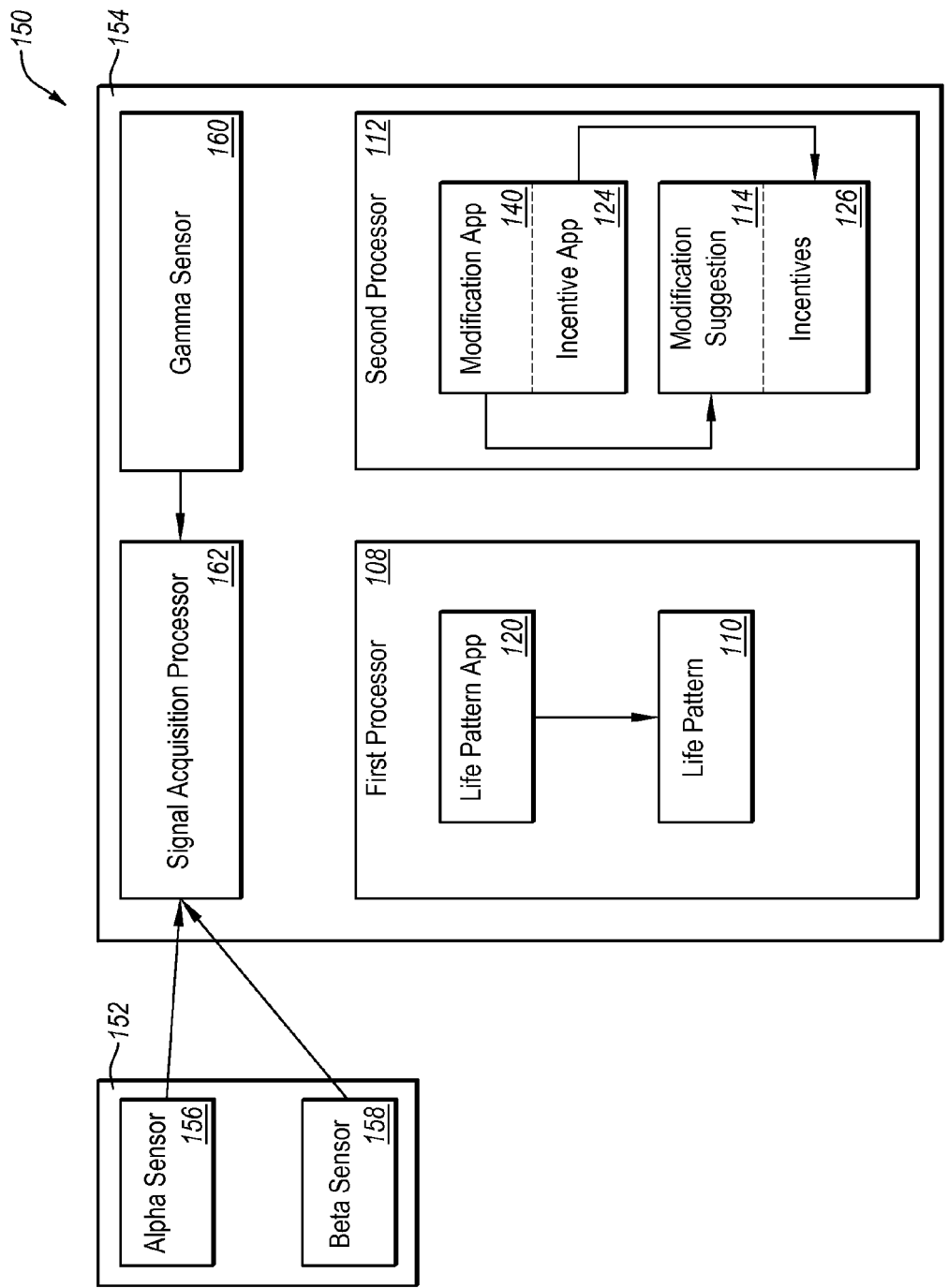
FIG. 1B illustrates an embodiment of the life pattern detection system of FIG. 1A implemented as a single device system.

In some embodiments of a life pattern detection system, such as the life pattern detection system 100 of FIG. 1A, a single device may have the capabilities of an acquisition device (described below with respect to FIGS. 2A and 2B), may incorporate one or more sensors, and may process input. An example of such a single device system is illustrated at 150 in FIG. 1B. As illustrated in FIG. 1B, the single device system 150 may include external sensors 152, and a multi-function device 154. In this example, the external sensors 152 are separate from the multi-function device 154. This example of the external sensors 152 may include an alpha sensor 156 and a beta sensor 158. The alpha sensor 156 and the beta sensor 158 are only illustrative and in no way limit a number of sensors included in the external sensors 152.

As further illustrated in FIG. 1B, the multi-function device 154 may include a gamma sensor 160 and a signal acquisition processor 162. In this example, the multi-function device 154, through inclusion of the signal acquisition processor 162, is capable of harvesting signals from the gamma sensor 160 which is local, as well as from the alpha sensor 156 and the beta sensor 158 which are remote from the multi-function device 154.

In some embodiments, the multi-function device 154 may be a "stand alone" device. The "stand alone" device does not include the external sensors 152 or any other hardware external to the multi-function device 154. For example, the multi-function device 154 may include the gamma sensor 160 and optionally other internal sensors (not shown). The signal acquisition processor 162 may harvest signals from the gamma sensor 160 and the other internal sensors. Additionally, the harvested signals may be provided to processors such as the first processor 108 and/or the second processor 112 of FIG. 1A.

As above, in the single device system 150 (i.e. including the external sensor 152 or as a "stand alone" device), the first processor 108 may execute the life pattern application 120 to generate a life pattern 110. The second processor 112 may execute the modification application 140 to generate modification suggestions 114 and/or the incentive application 124 to generate incentives 126. In this example, the modification suggestion 114 and the incentive 126 may be displayed at the multi-function device 154 or otherwise communicated to the user via the multi-function device 154, may be transmitted to the user, or may be transmitted to a server location where the user may access the modification suggestion 114 and incentive 126.

Alternatively, the multi-function device 154 may include some subset of these functions. For example, the multi-function device 154 may harvest signals from the gamma sensor 160, the alpha sensor 156, and the beta sensor 158 along with generating a local life pattern (not shown). The local life pattern may then be transmitted to the location of the second processor 112 to generate the modification suggestion 114 or the incentives 126. Additionally or alternatively, the multi-function device 154 may generate the local life pattern from the gamma sensor 160, the alpha sensor 156, and the beta sensor 158 and may further transmit the signals from these sensors to the location of an additional first processor 108 to generate a second life pattern (not shown) either based solely on the transmitted signals or the transmitted signals along with other input 104 as described with respect to FIG. 1A.

In some embodiments, the multi-function device 154 in the single device system 150 may communicate with a server (not shown). The server may include a server signal acquisition processor that may be similar to or identical to the signal acquisition processor 162. The server may be configured to receive sensor data generated by signals collected by the alpha sensor 156 and/or the beta sensor 158. The server may be further configured to analyze the received sensor data as described above with respect to the first processor 108 and/or the second processor 112. The server may then communicate results from the analysis to one or more multi-function device 154.

Alternatively, the server may receive the sensor data from the alpha sensor 156 and/or the beta sensor 158. Following reception of the sensor data from the alpha sensor 156 and/or the beta sensor 158, the server may store the sensor data for some time. The server may then sync with the multi-function device 154 and communicate the sensor data thereto.

The communication between the multi-function device 154 and the server may include communication of sensor data from multiple users and/or communication of analysis results. The communication between the multi-function device 154 and the server may enable analysis of sensor data 102 by the multi-function device 154 at the server. The communication between the multi-function device 154 and the server may be controlled by relative locations of the multi-function device 154 and/or the server, preset passwords, permissions, or any other mechanism that may enable secure communication.

Figure 2B:
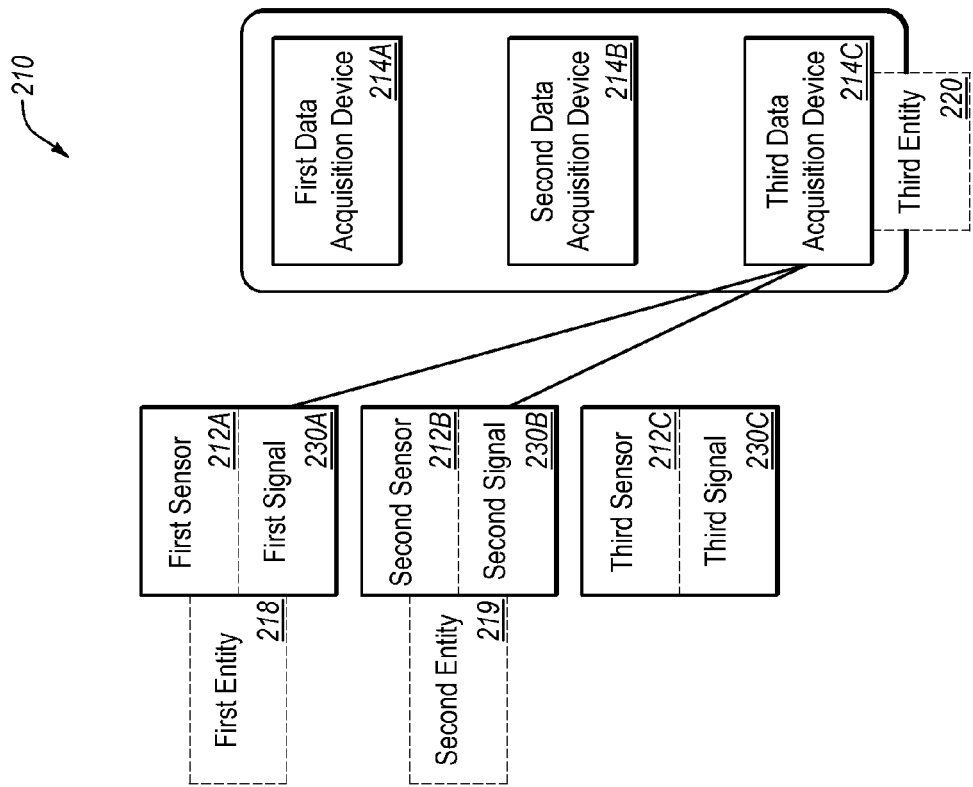
FIGS. 2A and 2B illustrate example architectures of sensor and signal acquisition systems that may be implemented in the life pattern detection systems of FIGS. 1A and 1B.
Figure 2A:
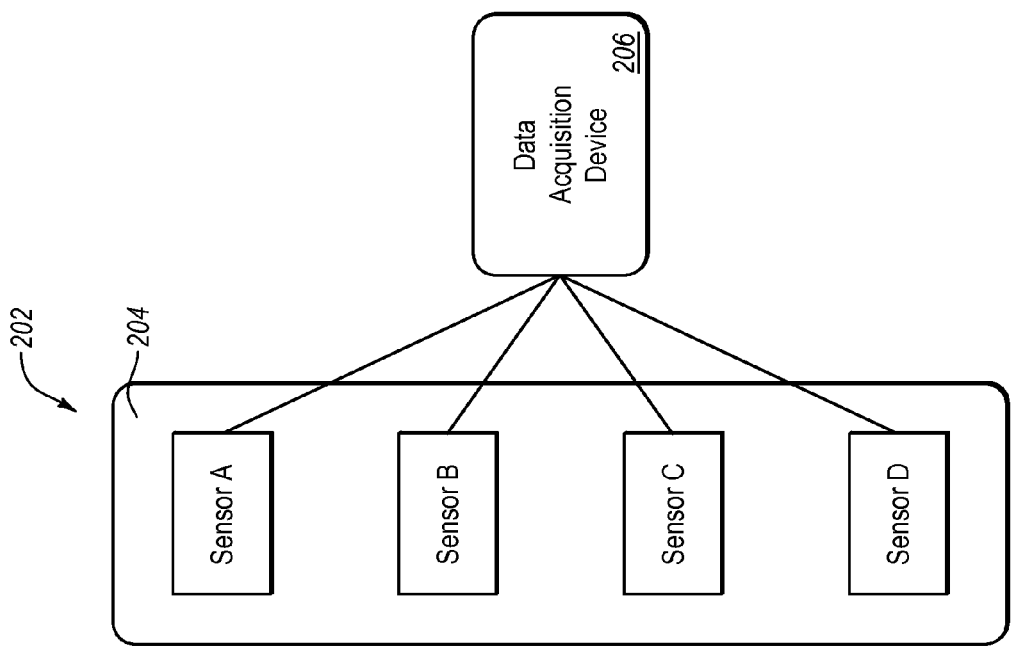

FIGS. 2A and 2B illustrate example architectures 202 and 210 of a sensor and signal acquisition system which may be implemented in the life pattern detection systems of FIGS. 1A and 1B. Specifically, FIG. 2A depicts a centralized architecture 202 and FIG. 2B depicts a distributed architecture 210.

Referring to FIG. 2A, the centralized architecture 202 includes a data acquisition device 206 and a set of sensors 204 (in FIG. 2A "Sensor A", "Sensor B", "Sensor C", and "Sensor D"). The set of sensors 204 measures physical quantities and converts the measurements to a first set of signals. The set of sensors 204 may additionally transmit the first set of signals. The acquisition device 206 may harvest, resolve, and synchronize the first set of signals.

Referring to FIG. 2B, the distributed architecture 210 generally allows multiple data acquisition devices 214A-214C to harvest, resolve, and synchronize some subset of sensor signals. The distributed architecture 210 includes a first sensor 212A, a second sensor 212B, and a third sensor 212C (generally, sensor 212 or sensors 212). Each of the sensors 212 measures a physical quantity and converts the measurements to a signal 230A-230C. Specifically, the first sensor 212A measures a first physical quantity which is converted to a first signal 230A, second sensor 212B measures a second physical quantity which is converted to a second signal 230B, and third sensor 212C measures a third physical quantity which is converted to a third signal 230C (generally, signal 230 or signals 230). In this example, the distributed architecture 210 includes three sensors. However, the distributed architecture 210 may include greater or fewer sensors 212 and correspondingly greater or fewer signals 230.

The distributed architecture 210 may also include the multiple data acquisition devices 214 including a first acquisition device 214A, a second acquisition device 214B, and a third acquisition device 214C (generally, acquisition device 214 or acquisition devices 214). The acquisition devices 214 and the acquisition device 206 of FIG. 2A may include a centralized server or a PED, or some component therein.

In a flexible form of the distributed architecture 210, any of the acquisition devices 214 may harvest any subset of signals 230 from any of the sensors 212. For example, the first acquisition device 214A may harvest a first signal 230A from the first sensor 212A. In addition, the second acquisition device 214B may harvest a second signal 230B from the second sensor 212B and may harvest a third signal 230C from the third sensor 212C. Each of the acquisition devices 214 may independently resolve and synchronize the harvested signals. That is, in this example, the first acquisition device 214A may resolve and synchronize the first signal 230A, and the second acquisition device 214B may resolve and synchronize the second signal 230B and the third signal 230C.

Additionally or alternatively, in some embodiments acquisition devices 214 may harvest the signals 230 based upon permissions, system configurations, or physical proximity to the sensors 212. In some embodiments, the data acquisition devices 214 may be owned by different entities 218-220. For example, the first sensor 212A may be owned and/or operated by a first entity 218, the second sensor 212B may be owned and/or operated by a second entity 219 and the third acquisition device 214C may be owned and/or operated by a third entity 220. Based upon permissions, system configurations, or physical proximity, acquisition devices 214 may harvest signals 214 owned and/or operated by other entities 218-220.

For example, the third acquisition device 214C may be included in a first multi-function device, such as the multi-function device 154 of FIG. 1B. The first multi-function device may be owned by a first user. Additionally, the first sensor 212A may be owned by a second user and the second sensor 212B may be owned by a third user. The third acquisition device 214C may harvest the first signal 230A from the first sensor 212A and the second signal 230B from the second sensor 212B. In FIG. 2B, the third acquisition device 214C harvesting the first signal 230A and the second signal 230B is represented by the lines connecting the first signal 230A and the second signal 230B with the third acquisition device 214C. The first signal 230A and second signal 230B may be resolved and synchronized at third acquisition device 214C.

In another example, the third acquisition device 214C may be included in the first multi-function device (discussed above). The first multi-function device may be owned by a first user. Additionally, the first sensor 212A may be owned by a second user and the second sensor 212B may be owned by a third user. The first signal 230A and/or the second signal 230B may be acquired by a server (not shown) and later harvested by the third acquisition device 214C from the server.

Additionally, in the distributed architecture 210, the signals 230 from multiple entities 218-220 may be combined or decoupled. For example, the first signal 230A and the second signal 230B may include information relating only to the first entity 218 or to the second entity 219. The third entity 220 may be interested in some subset of the information contained in the first signal 230A and/or the second signal 230B. The third entity 220 may accordingly decouple the first signal 230A and/or the second signal 230B such that only the subset of the first signal 230A and/or the second signal 230B, in which the third entity 220 is interested, is acquired by third acquisition device 214C.

The harvesting discussed with reference to the architectures 202 and 210 may be accomplished through near field communication (NFC), Bluetooth, ANT+ (ANT Plus), universal serial bus (USB) connection with servers, infrared, microwave, satellite transmission, or equivalent wireless or other communication standards or protocols. Additionally, the harvesting may occur at a sampling frequency (number of samples per unit of time). In either the centralized or the distributed architectures 202 or 210, the sampling frequency may adaptively slow to lower power consumption during certain periods or under certain circumstances.

Figure 3:
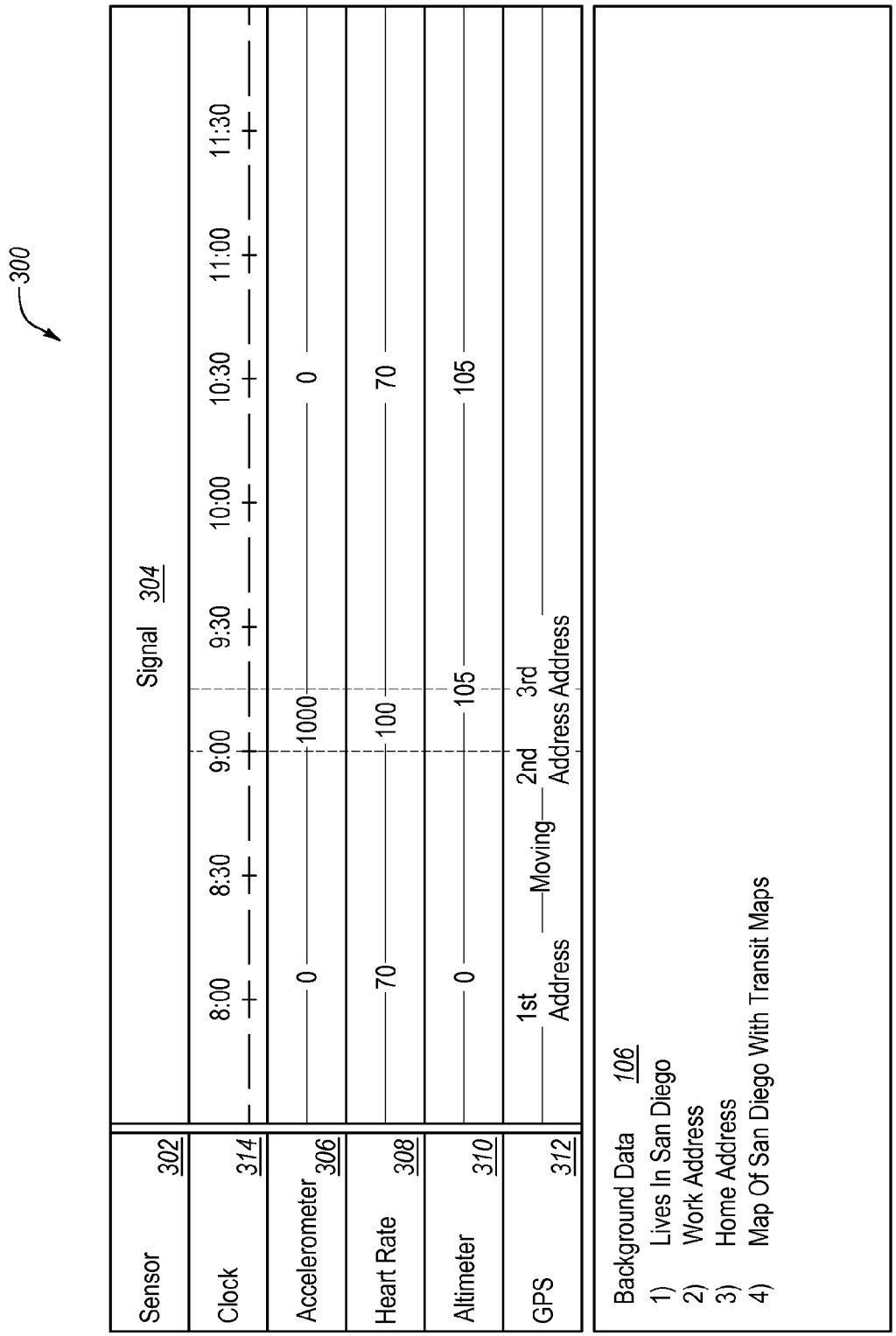
FIG. 3 illustrates an example data set that may be acquired using the life pattern detection systems of FIGS. 1A and 1B.

FIG. 3 illustrates an example data set 300 that may be acquired using the life pattern detection systems of FIGS. 1A and 1B. The life pattern 110 of FIGS. 1A-1B may be generated from the data set 300 using the life pattern application 120 of FIGS. 1A-1B, for instance. As illustrated in FIG. 3, the data set 300 includes a list of sensors 302. Specifically, in this example, the list of sensors 302 includes a clock 314, an accelerometer 306, a heart rate monitor 308, an altimeter 310, and a GPS receiver 312. The data set 300 further includes signals 304. The signals 304 are shown for each of the sensors in the list of sensors 302. Specifically, the clock 314 indicates the time beginning at 7:30 and ending at 12:00. The accelerometer 306 indicates that 0 steps were taken until 9:00 then 1000 steps were taken between 9:00 and 9:15 then 0 steps were taken between 9:15 and 12:00. The heart rate monitor 308 indicates a heart rate of 70 beats per minute (bpm) until 9:00, then between 9:00 and 9:15 the heart rate increased to 100 bpm, and after 9:15, the heart rate returned to 70 bpm. The altimeter 310 reads sea level until 9:15 then 105 feet above sea level between 9:15 and 12:00. The GPS receiver 312 reads a first address from 7:30 until 8:00, from 8:00 until 9:00 the GPS receiver 312 signal moves continuously, at 9:00 the GPS receiver reads a second address, and after 9:15 the GPS reads a third address. Additionally, this example data set 300 repeats Monday through Friday and does not occur on Saturday or Sunday (not shown in FIG. 3).

Also included in the data set 300 is an example of background data 106. In this example, the background data 106 includes user input indicating that the user lives in San Diego, the user has an office on the 5th floor, a work address, a residential address, and a map of San Diego including mass transit maps.

The data set 300 may be processed by the life pattern application 120 of FIG. 1A using the series of analytical steps discussed above which may include programmed templates that may be static or adaptive to determine the individual actions that generate a life pattern 110. For example with the data set 300, the following individual actions may be determined: First, the user begins at the first address. This individual action is determined from the user input address corresponding to the GPS signal for first address and the fact that the user is present at first address early in the morning. Second, the user commutes via the freeway, which takes an hour. This individual action is determined from the GPS receiver signal from 8:00 until 9:00 that moves continuously, tracks a freeway on the map of San Diego, and may not correspond to any mass transit route. Additionally, the user takes no steps during this period according to the accelerometer 306, the user's heart rate is 70 bpm indicating that the user is not running or bicycling, and the altimeter registers sea level indicating that the user is not taking an airplane or helicopter. Third, the user arrives at a parking space at the second address. This individual action is determined from the GPS signal indicating a second address that is neither the residential address nor the work address as well as the stop to the continuous movement attributed to a movement classification corresponding to driving a car. Fourth, the user walks from the parking lot to the user's work address. This individual action is indicated by the accelerometer 306 indicating 1000 steps between 9:00 and 9:15. This individual action is confirmed by the relative distance between the second address and the third address which takes 15 minutes and produces a heart rate of 100 bpm during the activity. The relatively few steps and possibly a cadence derived from the signal of the accelerometer 306, the slow pace, and the low heart rate indicate a leisurely walk. Fifth, the user arrives at third address which is the user's work address. This individual action is determined from the user input address corresponding to the GPS signal for third address and the fact that the user is present at the third address from 9:15 until at least 12:00 Monday through Friday and not Saturday and Sunday. Sixth, the user takes the elevator from the lobby to the fifth floor. This individual action is indicated by the change in altitude at 9:15 without taking any steps as indicated by the pedometer and maintaining this altitude until at least 12:00.

Figure 4:
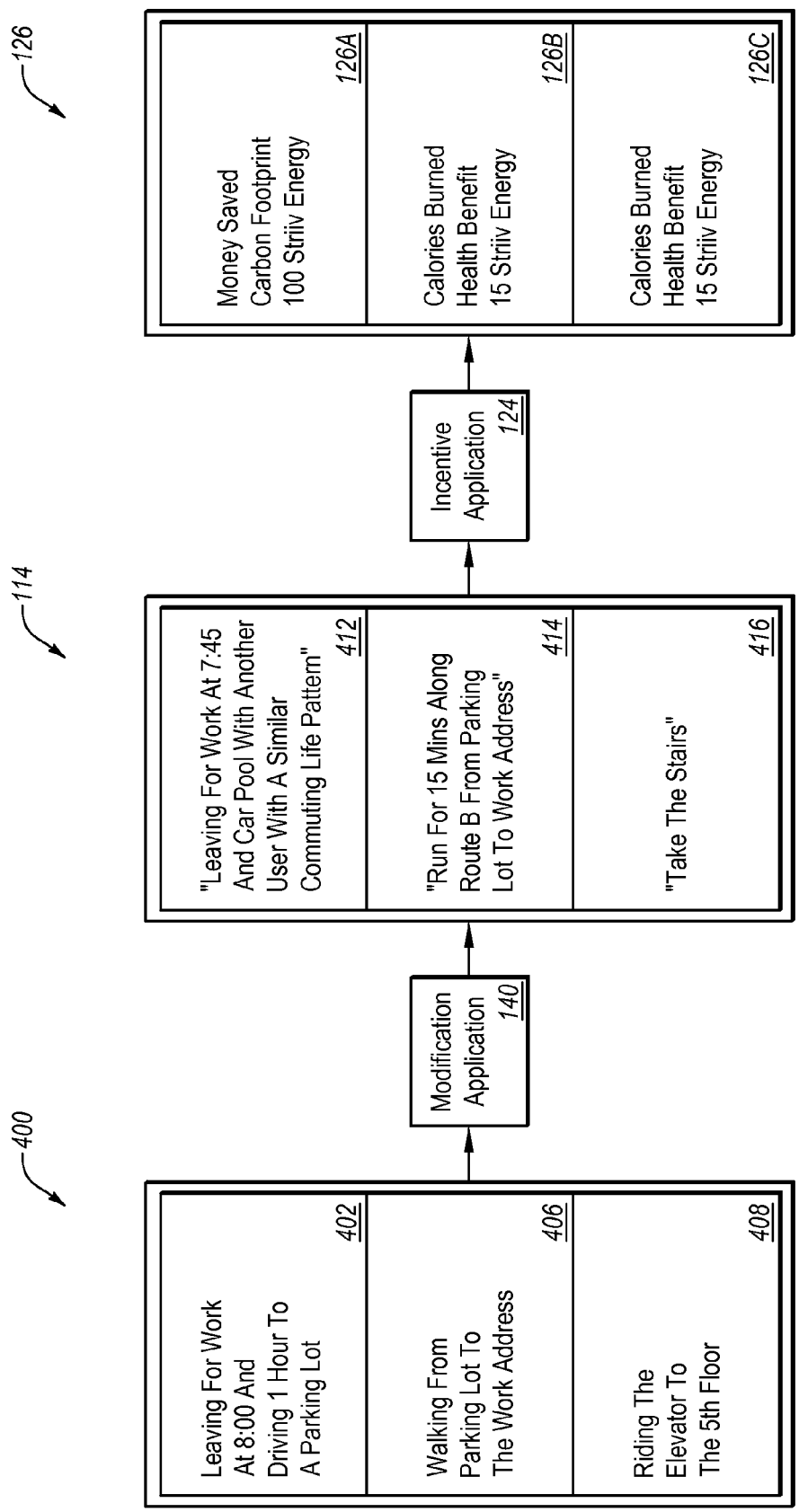
FIG. 4 illustrates an example life pattern that may be generated from the data set of FIG. 3.

FIG. 4 illustrates an example life pattern 400 that may be generated from the data set 300 of FIG. 3 as well as the application of the modification application 140 and the incentive application 124 to the life pattern 400. With combined reference to FIGS. 3 and 4, the data set 300 indicates the following sequence of individual actions and generates a commuting life pattern 400 including: 402 leaving for work at 8:00 and driving 1 hour to a parking lot, 406 walking from the parking lot to the work address, 408 riding the elevator up to the fifth floor and working.

Generally, the modification application 140 receives the life pattern 110 and performs an analysis to generate modification suggestions 114. The modification application 140 processes each individual action along with obtaining information that can be used to generate a corresponding modification suggestion 114. For example, in the commuting life pattern 400 shown in FIG. 4, the following modification suggestions 114 may be generated: First, corresponding to the activity leaving for work at 8:00 and driving 1 hour to the parking lot 402, the modification suggestion 114 may be "leave for work at 7:45 and car pool with another user with a similar commuting life pattern" 412. To make this modification suggestion 114, the modification application 140 may have obtained information such as other users' commuting life patterns, the anticipated change in overall commuting time, and perhaps downloaded websites that post ride-share or vanpool information. Second, corresponding to the activity of walking from the parking lot to work 406, the modification suggestion 114 may be "run for the fifteen minutes along Route B from the parking lot to the work address" 414. To make this modification suggestion 114, the modification application 140 may have obtained the local topographical area, the user's personal fitness goals, and the user's personal health information, for instance. Third, corresponding to the activity of riding the elevator up to the fifth floor 408, the modification suggestion 114 may be "take the stairs" 416. To make this modification suggestion 114, the modification application 140 may have obtained a blue print of the building located at the work address or may be programmed to automatically determine that buildings with elevators will also have stairs based on known building codes.

As further illustrated in FIG. 4, the incentive application 124 may generate incentives 126 corresponding to each modification suggestions 114 (e.g., 412, 414, and 416 in FIG. 4). For example, in the commuting life pattern 400 shown in FIG. 4, the following incentives 126 may be generated. First, corresponding to the modification suggestion 114 "leave for work at 7:15 and car pool with another user with a similar commuting life pattern" 412, a first incentive 126A may include a calculation and communication of the money saved, environmental benefit such as the reduced carbon emission, or may include points in a game or virtual currency such as Striiv energy. Second, corresponding to the modification suggestion 114 of "run for the fifteen minutes along Route B from the parking lot to the work address" 414, a second incentive 126B may include a calculation of the calories burned and resultant health benefits, or may further include points in a game or virtual currency such as Striiv energy. Third, corresponding to the modification suggestion 114 of "take the stairs" 416, a third incentive 126C may include a calculation of the calories burned and health benefits, or may include points in a game or virtual currency such as Striiv energy.

Additionally, the modification application 140 and the incentive application 124 may take into consideration completion of past modification suggestions 114, referred to as uptakes, to generate future modification suggestions 114 and/or incentives 126. In the example above, if modification suggestion 114 of "take the stairs" 416 is not completed in the commuting life pattern 400, the modification application 140 may generate an alternative modification suggestion 114 for the commuting life pattern 400 and/or may modify the first incentive 126A such as increasing offered points in a game or virtual currency such as Striiv energy. If however, the modification suggestion 114 of "take the stairs" 416 was completed, the modification application 140 may generate similar modification suggestions 114 and/or the incentive application 124 may generate similar incentives 126 in other life patterns.

Additionally, the modification application 140 and the incentive application 124 may correlate uptakes with other data from the data set (not shown). The modification application 140 and the incentive application 124 may use the correlation between uptakes and other data from the data set to modify the types of modification suggestions 114 and incentives 126 that are generated.

In the example above, if the modification suggestion 114 of "take the stairs" 416 is not completed and further the modification suggestion 114 "run for the fifteen minutes along Route B from the parking lot to the work address" 414 is not completed but similar modification suggestions are completed in a life pattern related to weekend activities, then the modification application 140 and the incentive application 124 may determine that modification suggestions 114 encouraging exercise are not effective on weekdays but are effective on weekends. Thus, the modification application 140 and the incentive application 124 may modify the modification suggestions 114 to no longer encourage exercise on weekdays.

Figure 5:
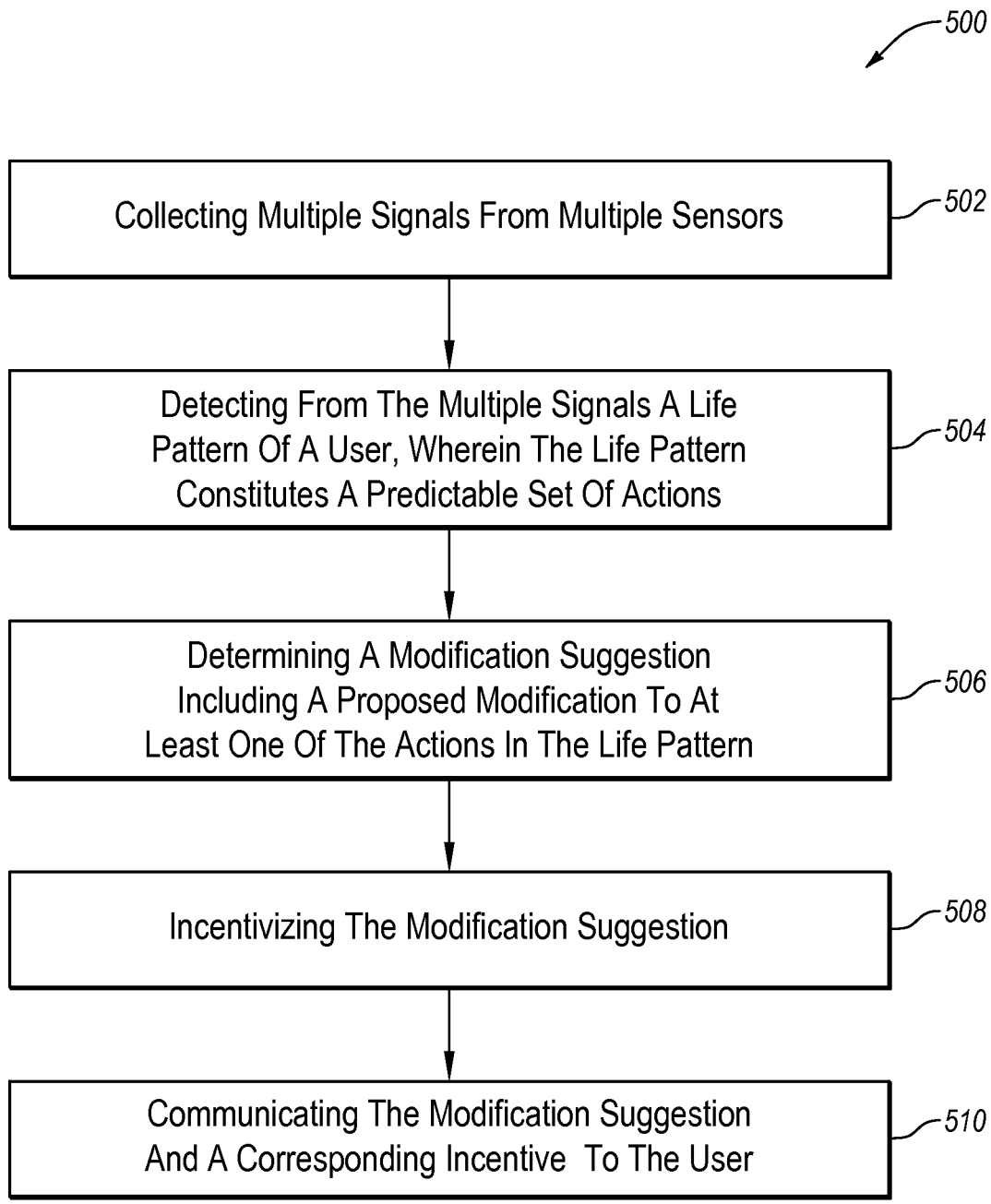
FIG. 5 is a flow chart illustrating an example method of determining a life pattern that may be implemented by the life pattern detection systems of FIGS. 1A and 1B.

FIG. 5 is a flow chart illustrating an example method 500 of determining a life pattern. The method 500 may be implemented by the life pattern detection systems of FIGS. 1A and 1B in some embodiments. One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

The method may begin at block 502 in which multiple signals are collected from multiple sensors. In some embodiments, collecting the multiple signals may include collecting the multiple signals in a distributed sensor architecture. The distributed sensor architecture may be configured such that each of the sensors is periodically synchronized and harvested.

Additionally or alternatively, the multiple sensors may include at least one internal sensor and at least one external sensor. The internal sensor and the external sensor may be variously owned and/or operated by separate entities.

At block 504, the method 500 may include detecting from the multiple signals a life pattern of a user. The life pattern may constitute a predictable set of actions. In some embodiments detecting the life pattern may include organizing multiple signals by sensor type; time sequencing the multiple signals; sequencing the multiple signals by positional coordinates; extracting signals consistent with an identifiable action; monitoring for repeating and/or predictable patterns, or any combination thereof.

At block 506, the method 500 may include determining a modification suggestion. The modification suggestion may include a proposed modification to at least one of the actions in the life pattern. In some embodiments determining the modification suggestion may include organizing the multiple signals into identifiable actions; determining whether a substitute action exists; downloading background data; requesting additional information from the user; examining the user's personal goals, or any combination thereof. Additionally in some embodiments, the modification suggestion may be configured to provide the user with a health benefit.

At 508, the method 500 may include incentivizing the modification suggestion. In some embodiments, incentivizing the modification suggestion may conform to a game application, a virtual economy, a personal incentive program, or a social networking application. Additionally or alternatively, the incentivizing the modification may encourage a health benefit for the user or may incorporate a commercial sponsorship.

At block 510, the method 500 may include communicating the modification suggestion and/or a corresponding incentive to the user. Additionally or alternatively, the modification suggestion and/or the corresponding incentive may be communicated to a web application or a storage location. The user may have access to the web application and/or the storage location such that the user may view the modification suggestion and/or the corresponding incentive.

In some embodiments, generation of the modification suggestion and/or the incentive may take into consideration completion of past modification suggestions to generate future modification suggestions and/or incentives. In these embodiments, the completion of past modification suggestions may be referred to as uptakes. For example, based on uptakes, a future modification suggestion may modify a different action included in a life pattern, may incentivize an uncompleted modification suggestion with an incentive from a completed modification suggestion, etc.

Additionally, in some embodiments uptakes may be correlated with other data from other data sets. The other data sets may be generated by other users, from other sensors, from other life patterns, etc. Future modification suggestions and incentives may be generated using the correlation between the uptakes and the other data.

The embodiments described herein may include the use of a special purpose or general-purpose computer including various computer hardware or software modules, as discussed in greater detail below.

Embodiments within the scope of the present invention also include tangible computer-readable media for carrying or having computer-executable instructions or data structures stored thereon. Such computer-readable media can be any available media that can be accessed by a general purpose or special purpose computer. By way of example, and not limitation, such computer-readable media can include non-transitory computer-readable storage media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

Figure 6:
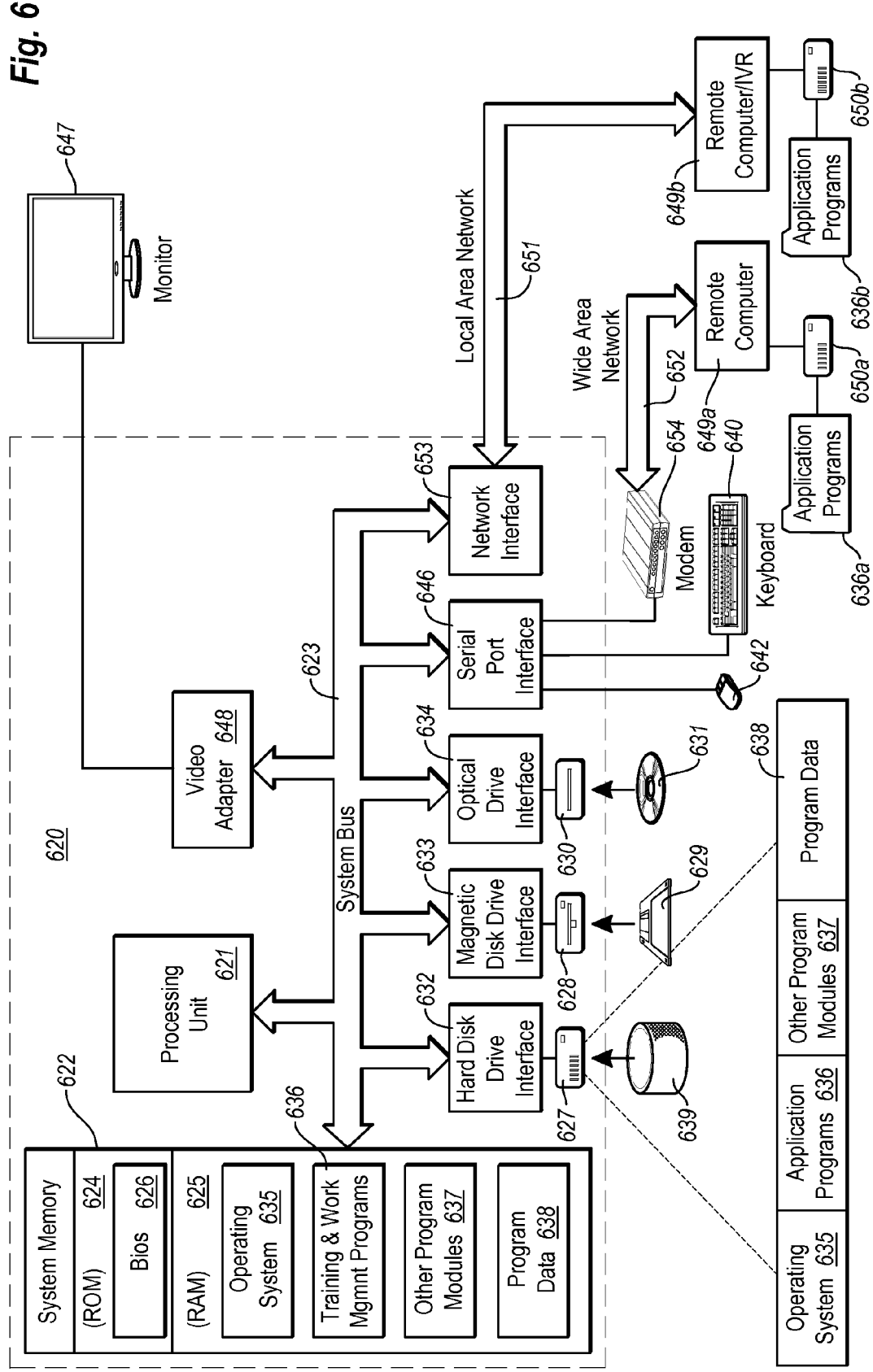
FIG. 6 provides a brief, general description of a suitable computing environment in which several embodiments may be implemented.

FIG. 6 and the following discussion are intended to provide a brief, general description of a suitable computing environment in which several embodiments may be implemented. For example, FIG. 6 may illustrate an example of various components of a server or PED that can perform some or all of the steps and operations described herein. Although not required, several embodiments will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps disclosed herein.

Those skilled in the art will appreciate that the embodiments illustrated herein may be practiced in network computing environments with many types of computer system configurations, including personal computers, hand-held devices, multi-processor systems, microcontroller-based or programmable consumer electronics, network PCs, mini-computers, mainframe computers, and the like. Several embodiments may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 6, an example of a computer system for implementing several embodiments relating to life pattern detection, modification suggestions and/or incentives is illustrated, which includes a general purpose computing device in the form of a conventional computer 620, including a processing unit 621, a system memory 622, and a system bus 623 that couples various system components including the system memory 622 to the processing unit 621. The system bus 623 may be any of several types of bus structures including a memory bus or memory controller, a peripheral bus, and a local bus using any of a variety of bus architectures. The system memory includes read only memory (ROM) 624 and random access memory (RAM) 625. A basic input/output system (BIOS) 626, containing the basic routines that help transfer information between elements within the computer 620, such as during start-up, may be stored in ROM 624. Such components, or similar components, may also embody a workstation for a company representative.

The computer 620 may also include a magnetic hard disk drive 627 for reading from and writing to a magnetic hard disk 639, a magnetic disk drive 628 for reading from or writing to a removable magnetic disk 629, and an optical disk drive 630 for reading from or writing to removable optical disk 631 such as a CD-ROM, DVD, or other optical media. The magnetic hard disk drive 627, magnetic disk drive 628, and optical disk drive 630 are connected to the system bus 623 by a hard disk drive interface 632, a magnetic disk drive-interface 633, and an optical drive interface 634, respectively. The drives and their associated computer-readable media provide non-volatile storage of computer-executable instructions, data structures, program modules and other data for the computer 620. Although the environment described herein employs a magnetic hard disk 639, a removable magnetic disk 629 and a removable optical disk 631, other types of computer readable media for storing data can be used, including magnetic cassettes, flash memory cards, digital versatile disks, Bernoulli cartridges, RAMs, ROMs, millipede memory, and the like.

Program code means comprising one or more program modules may be stored on the hard disk 639, magnetic disk 629, optical disk 631, ROM 624 or RAM 625, including an operating system 635, one or more life pattern, modification, or incentive applications 636, other program modules 637, and program data 638, such as sensor data 102, background data 106, life pattern data 110, modification suggestions 114, and/or incentives 126 (see FIG. 1). A user may enter commands and information into the computer 620 through keyboard 640, pointing device 642, or other input devices (not shown), such as a microphone, joy stick, game pad, satellite dish, scanner, touch screen display, or the like. These and other input devices are often connected to the processing unit 621 through a serial port interface 646 coupled to system bus 623. Alternatively, the input devices may be connected by other interfaces, such as a parallel port, a game port, or a universal serial bus (USB). A monitor 647 or another display device is also connected to system bus 623 via an interface, such as video adapter 648. In addition to the monitor, personal computers and other electronic devices typically include other peripheral output devices (not shown), such as speakers and printers.

The computer 620 may operate in a networked environment using logical connections to one or more remote computers, such as remote computers 649a and 649b. Remote computers 649a and 649b may each be another personal computer, a server, a router, a network PC, a peer device or other common network node, and typically include many or all of the elements described above relative to the computer 620, although only memory storage devices 650a and 650b and their associated application programs 636a and 636b have been illustrated in FIG. 6. The logical connections depicted in FIG. 6 include a LAN 651 and a WAN 652 that are presented here by way of example and not limitation. Such networking environments are commonplace in intranets and the Internet.

When used in a LAN networking environment, the computer 620 is connected to the local network 651 through a network interface or adapter 653. When used in a WAN networking environment, the computer 620 may include a modem 654, a wireless link, or other means for establishing communications over the wide area network 652, such as the Internet. The modem 654, which may be internal or external, is connected to the system bus 623 via the serial port interface 646. In a networked environment, program modules depicted relative to the computer 620, or portions thereof, may be stored in the remote memory storage device. It will be appreciated that the network connections shown are exemplary and other means may be provided for establishing communications over wide area network 652 or local area network 651 for acquiring signals/data from sensors or data acquisition devices, transmitting modification suggestions/incentives to a user, and so on.

The present invention may be embodied in other specific forms without departing from its spirit. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A life pattern detection system comprising:
a sensor configured to monitor actions of a user;
a data acquisition device configured to harvest signals from the sensor and produce sensor data;
a first processor configured to:
 receive the sensor data and background data, and
 execute a life pattern application including a first series of analytical steps that determines a predictable set of actions from the sensor data and the background data;
a plurality of sensors that include the sensor;
a first personal electronic device (PED) including a first subset of the plurality of sensors and the first processor; and
a second PED including a second subset of the plurality of sensors and a second processor including a second life pattern application, wherein:
the first subset of the plurality of sensors and the second subset of the plurality of sensors are configured to monitor actions of the user;
the first PED and the second PED independently receive and process sensor data from the respective subsets of sensors, and
the first processor and the second processor are configured to execute the respective life pattern applications to determine a predictable set of actions from the sensor data.

2. The system of claim 1, further comprising:
a second processor configured to:
receive the predictable set of actions from the first processor, and
execute a modification application including a second series of analytical steps that determine a modification suggestion to alter an action included in the predictable set of actions; and
a modification transmitter configured to transmit the modification suggestion to the user.

3. The system of claim 2, wherein the modification transmitter is further configured to transmit the modification suggestion to a storage location that is accessible by the user or to transmit the modification suggestion to a web application.

4. The system of claim 2, further comprising:
a hybrid synchronous interface that dictates transmission timing of the modification suggestions according to a periodic time interaction with the user and real time interaction with the user.

5. The system of claim 2, wherein the second series of analytical steps includes:
organizing the sensor data into identifiable actions;
determining whether an substitute action exists;
downloading additional background data;
requesting additional information from the user; and
examining personal goals of the user.

6. The system of claim 2, wherein the second processor is further configured to execute an incentive application that generates an incentive for the modification suggestion and wherein the modification transmitter is configured to transmit the incentive to the user.

7. The system of claim 6, further comprising a server including the first processor and/or the second processor, wherein at least some portion of the sensor data is communicated to the server and at least one of the life pattern application, the modification applications, or the incentive application is executed at the server.

8. The system of claim 6, wherein the incentive conforms to a game application, a virtual economy, a personal incentive program, or a social networking application.

9. The system of claim 6, wherein the modification suggestion and the incentive encourage a health benefit for the user or incorporate a commercial sponsorship.

10. The system of claim 1, wherein the first processor is further configured to receive and process sensor data from the second subset of sensors and to aggregate the sensor data from the first subset of sensors and the second subset of sensors.

11. The system of claim 10, wherein the first series of analytical steps comprises:
organizing the sensor data into types of sensor signals;
time sequencing the sensor data;
sequencing the sensor data by positional coordinates;
extracting signals consistent with an identifiable action;
fitting the sensor data to the background data;
monitoring for predictable patterns; and
eliminating the sensor data that is erroneous or conflicting combinations of sensor data.

12. A multi-function device comprising:
an internal sensor configured to sense actions of a user;
a signal acquisition processor configured to harvest sensor data from the internal sensor;
a first processor configured to determine a predictable set of actions from the sensor data;
a second processor configured to determine a modification suggestion to alter an action included in the predictable set of actions and to generate an incentive corresponding to the modification suggestion; and
a display configured to display the modification suggestion and the incentive to the user;
wherein the first processor includes a microcontroller and a main processor, and wherein the microprocessor is configured to:
operate at a lower power consumption level than the main processor,
monitor the internal sensors while the main processor operates in a sleep state, and
at a threshold signal of the internal sensor, trigger the main processor to restore the main processor to an active state.

13. The multi-function device of claim 12, wherein the signal acquisition processor is further configured to harvest sensor data from an external sensor that is separate from the multi-function device.

14. The multi-function device of claim 13, wherein the external sensor is owned and/or operated by a separate entity than the multi-function device and harvesting sensor data from the external sensor is controlled by a permission.

15. The multi-function device of claim 12, further comprising a transmitter configured to transmit the modification suggestion and the incentive to a server location configured such that the user can access the modification suggestion and the incentive.

16. A method of determining a life pattern for the purpose of altering behavior comprising:
collecting a plurality of signals from a plurality of sensors, including collecting a plurality of signals from a plurality of sensors in a distributed sensor architecture in which each sensor of the plurality of sensors is periodically synchronized and harvested;
detecting from the plurality of signals a life pattern of a user, wherein the life pattern constitutes a predictable set of actions;
determining a modification suggestion including a proposed modification to at least one of the actions in the life pattern;
incentivizing the modification suggestion; and
communicating the modification suggestion and a corresponding incentive to the user.

17. The method of claim 16, wherein the modification suggestion is configured to provide the user with a health benefit.

18. The method of claim 16, wherein the plurality of sensors comprises at least one internal sensor and at least one external sensor variously owned and/or operated by separate entities.

19. The method of claim 16, wherein detecting the life pattern comprises:
organizing the plurality of signals by sensor type;
time sequencing the plurality of signals;
extracting signals consistent with an identifiable action; and
monitoring for predictable patterns.

20. The method of claim 16, wherein detecting the life pattern comprises:

sequencing the plurality of signals by positional coordinates.

* * * * *